United States Patent
Liu et al.

(10) Patent No.: US 12,398,408 B2
(45) Date of Patent: Aug. 26, 2025

(54) **RECOMBINANT *Escherichia coli* FOR PRODUCING GLUTARATE, CONSTRUCTION METHOD AND USE THEREOF**

(71) Applicant: JIANGNAN UNIVERSITY, Wuxi (CN)

(72) Inventors: Liming Liu, Wuxi (CN); Zhilan Zhang, Wuxi (CN); Cong Gao, Wuxi (CN); Xiulai Chen, Wuxi (CN); Liang Guo, Wuxi (CN); Jia Liu, Wuxi (CN); Wei Song, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 0 days.

(21) Appl. No.: 17/640,807

(22) PCT Filed: Dec. 3, 2021

(86) PCT No.: PCT/CN2021/135262
§ 371 (c)(1),
(2) Date: Jun. 1, 2023

(87) PCT Pub. No.: WO2023/092632
PCT Pub. Date: Jun. 1, 2023

(65) Prior Publication Data
US 2024/0043884 A1    Feb. 8, 2024

(30) Foreign Application Priority Data

Nov. 29, 2021 (CN) .......................... 202111433195.5

(51) Int. Cl.
| | | |
|---|---|---|
| C12P 7/44 | (2006.01) | |
| C12N 1/21 | (2006.01) | |
| C12N 9/02 | (2006.01) | |
| C12N 9/06 | (2006.01) | |
| C12N 9/88 | (2006.01) | |
| C12N 15/70 | (2006.01) | |

(52) U.S. Cl.
CPC .............. *C12P 7/44* (2013.01); *C12N 9/0008* (2013.01); *C12N 9/0022* (2013.01); *C12N 9/88* (2013.01); *C12N 15/70* (2013.01); *C12Y 102/01005* (2013.01); *C12Y 104/03004* (2013.01); *C12Y 401/01028* (2013.01); *C12N 2800/101* (2013.01)

(58) Field of Classification Search
None
See application file for complete search history.

(56) References Cited

FOREIGN PATENT DOCUMENTS

| CN | 108753636 A | 11/2018 |
|---|---|---|
| CN | 111849845 A | 10/2020 |
| CN | 112226398 A | 1/2021 |
| WO | 2005089505 A2 | 9/2005 |

OTHER PUBLICATIONS

Torrens-Spence et al., Biochemical evaluation of a parsley tyrosine decarboxylase results in a novel 4-hydroxyphenylacetaldehyde synthase enzyme, Biochemical Biophysical Res. Comm. 418, 2012, 211-16. (Year: 2012).*
Torrens-Spence et al., Biochemical Evaluation of the Decarboxylation and Decarboxylation-Deamination Activities of Plant Aromatic Amino Acid Decarboxylases, JBC 288, 2013, 2376-87. (Year: 2013).*
Zhang et al., Systems engineering of Escherichia coli for high-level glutarate production from glucose, Nature Comm. 15, 2024, 1032. (Year: 2024).*
Jiaping Wang et a., "Engineering the Cad pathway in *Escherichia coli* to produce glutarate from L-lysine" Applied Microbiology and Biotechnology (2021) 105:3587-3599 (Apr. 27, 2021).
Jiaping Wang et al., "Expanding the lysine industry: biotechnological production of L-lysine and its derivatives" Advances in Applied Microbiology, vol. 115, pp. 1-33 (Mar. 18, 2021).
Wenna Li et al., "Targeting metabolic driving and intermediate influx in lysine catabolismfor high-level glutarate production" Nature Communications, vol. 10, No. 1, article 3347 (Jul. 26, 2019).
Jiaojiao Zeng et al., "Metabolic engineering of Escherichia coli for improving tyrosol production" Food and Fermentation Industries,2021,47(22): 8-15 (Apr. 28, 2021).
Z. Yin et al., NP_000373.1, Aldehyde dehydrogenase family 3 member A2 isoform 2 (*Homo sapiens*], Genbank database (Nov. 26, 2021).

* cited by examiner

*Primary Examiner* — Todd M Epstein
(74) *Attorney, Agent, or Firm* — SZDC Law PC

(57) ABSTRACT

The present invention provides recombinant *Escherichia coli* for producing glutarate, a construction method and use thereof. A double-plasmid recombinant bacterium is constructed through molecular biological means for co-expressing an aldehyde synthase (AAS) gene, an amine oxidase Mao (gene) and an aldehyde dehydrogenase (Glox) gene. The constructed expression plasmids are introduced into the *Escherichia coli* to reconstruct to obtain recombinant cells. A recombination strain for efficiently producing glutarate is obtained through amicillin resistance and kanamycin resistance combined plate screening. Efficient production of the glutarate is achieved by optimizing concentration of a substrate, cell concentration and a transformation temperature. L-lysine with a concentration of 30 g/L may be transformed into 19.65 g of glutarate through reactions for 30 h under transformation conditions that the cell concentration is 30 g/L, the pH value is 8 and 6 mM of $NAD^+$ is additionally added, wherein a transformation rate may be 65.3%.

10 Claims, 3 Drawing Sheets

Specification includes a Sequence Listing.

RECOMBINANT Escherichia coli FOR PRODUCING GLUTARATE, CONSTRUCTION METHOD AND USE THEREOF This application is the National Stage Application of PCT/CN2021/135262, filed on Dec. 3, 2021, which claims priority to Chinese Patent Application No. 202111433195.5, filed on Nov. 29, 2021, which is incorporated by reference for all purposes as if fully set forth herein.

FIELD OF THE INVENTION

The present invention relates to the technical field of metabolic engineering, and more particularly to a recombinant Escherichia coli for efficiently producing glutarate, and a construction method and use thereof.

DESCRIPTION OF THE RELATED ART

Glutarate, commonly known as colloidal acid, is an aliphatic dicarboxylic acid with a molecular formula of $C_5H_8O_4$ and a molecular weight of 132.11. It is a colorless needle-like crystalline solid at the room temperature, and is freely soluble in water, ethanol, ether, etc., with solubility in water of 430 g/L. Among all dicarboxylic acids, the glutarate is more suitable for production of polyesters and polyamides of nylon-4,5 and nylon-5,5 and the like due to the lowest melting point of 95-98° C. In addition, the glutarate is also a precursor of 1,5-pentanediol which is a common plasticizer of a soldering flux, an activator and an important medical intermediate. In short, the glutarate, as an important C5 platform compound, has an important application value and a development potential in the fields of medicine, chemical synthesis, and the like.

At present, the main preparation method of the glutarate is a chemical synthesis method, in which industrial production mainly refers to recycling from a mixture of oxidized cyclohexanone and cyclohexanol under the catalysis of nitric acid. A small dose of glutamate also can be prepared at the laboratory level, for example, the glutarate is prepared through a series of chemical reactions by taking γ-butyrolactone, dihydropyran, glutaronitrile, cyclohexanone and the like as a substrate. The conventional chemical method for synthesizing the glutarate has the disadvantages of high cost, severe pollution, high requirements on operation conditions, and the like. As a result, it is of profound significance in environmental protection, efficient production and a good production prospect of the glutarate in the future.

In recent years, domestic and foreign researchers have explored and researched the production of the glutarate by microorganisms from two aspects: biochemical engineering and metabolic engineering. So far, there are four biosynthetic pathways of the glutarate reported in the literature, namely: a glutaconate reduction pathway, a carbon chain extension and decarboxylation pathway, a reverse adipate-degradation pathway, and a lysine degradation pathway (including a degradation pathway with pentane diamine as an intermediate and a degradation pathway with 5-aminovaleric acid as an intermediate). All of the pathways adopt excessive enzymes and are too complex. Therefore, how to construct a brand-new and shortest pathway to improve the yield of the glutarate has become an urgent problem to be solved, and it is also one of the research hotspots worldwide.

SUMMARY OF THE INVENTION

To solve the technical problems, the present invention provides a brand-new pathway for producing glutarate, and the effectiveness of the pathway is verified by constructing a single enzyme expression strain. The present invention further provides a recombinant Escherichia coli engineering bacterium for efficiently producing glutarate. By constructing a double-plasmid expression system, a gene AAS for coding aromatic aldehyde synthase, a gene Mao for coding amine oxidase and a gene Glox for coding aldehyde dehydrogenase are co-expressed in a host of the Escherichia coli to obtain a recombinant bacterium. By taking the constructed recombinant bacterium as a catalyst and L-lysine as a substrate to achieve catalyzed synthesis of the glutarate, the reaction conditions are optimized.

A first object of the present invention is to provide recombinant Escherichia coli for producing glutarate. The recombinant Escherichia coli is obtained by expressing the aromatic aldehyde synthase (AAS) gene, the amine oxidase (Mao) gene and the aldehyde dehydrogenase (Glox) gene in the host of Escherichia coli.

In the present invention, a specifically constructed metabolic reaction path includes transforming the L-lysine into 5-amino valeraldehyde through the aromatic aldehyde synthase (AAS), transforming the 5-amino valeraldehyde into glutaraldehyde through the amine oxidase (Mao) and transforming the glutaraldehyde into the glutarate through the aldehyde dehydrogenase (Glox).

Preferably, the aromatic aldehyde synthase (AAS) gene, the amine oxidase (Mao) gene and the aldehyde dehydrogenase (Glox) gene are expressed through the double-plasmid expression system.

Preferably, the aromatic aldehyde synthase gene and the amine oxidase gene are expressed through the same plasmid.

Preferably, the double-plasmid expression system is a combination of two of a pETM6R1 plasmid, pET28a plasmid, a PRSF plasmid, a pCOR plasmid, a pCDF plasmid and a PACYC plasmid.

In the present invention, in a specific embodiment: the pETM6R1 plasmid is used for expressing the aromatic aldehyde synthase (AAS) gene and the amine oxidase (Mao) gene, and the pET28a plasmid is used for expressing the aldehyde dehydrogenase (Glox) gene.

Preferably, an amino acid sequence of the aromatic aldehyde synthase is as shown in SEQ ID NO:1, an amino acid sequence of the amine oxidase (Mao) is as shown in SEQ ID NO:2, and an amino acid sequence of the aldehyde dehydrogenase (Glox) is as shown in SEQ ID NO:3.

Preferably, the host of the Escherichia coli is E. coli BL21 (DE3), E. coli JM109 (DE3) or E. coli MG1655 (DE3).

A second object of the present invention is to provide a construction method of the recombinant Escherichia coli, including the following steps:

S1, ligating the aromatic aldehyde synthase (AAS) gene and the amine oxidase (Mao) gene to a first vector to obtain a first recombinant vector;

S2, ligating the aldehyde dehydrogenase (Glox) gene to a second vector to obtain a second recombinant vector; and S3, introducing the first recombinant vector and the second recombinant vector into the host of the Escherichia coli to screen a recombinant bacterium, which is capable of expressing the aromatic aldehyde synthase (AAS) gene, the amine oxidase (Mao) gene and aldehyde dehydrogenase (Glox) gene.

In the present invention, in a specific embodiment: a coding gene of the aromatic aldehyde synthase (AAS) with the amino acid sequence as shown in SEQ ID NO:1 and a coding gene of the amine oxidase (Mao) with the amino acid sequence as shown in SEQ ID NO:2 are ligated to a pETM6R1 vector through enzyme digestion after being amplified, to finally construct a plasmid pETM6R1-AAS-Mao. The aldehyde dehydrogenase (Glox) gene with the amino acid sequence shown in SEQ ID NO:3 is ligated to the pET28a vector through the enzyme digestion after being amplified, to finally construct a plasmid pET28a-Glox. The two plasmids are simultaneously introduced into the *E. coli* MG1655 (DE3) to express.

A third object of the present invention is to provide use of the recombinant *Escherichia coli* in producing the glutarate.

Preferably, a whole-cell of the recombinant *Escherichia coli* is taken as a catalyst for transforming L-lysine to produce the glutarate.

Preferably, in a transformation system, the additive amount of the L-lysine is 20-50 g/L.

Preferably, the transformation system further includes 4-8 mM of $NAD^+$.

Preferably, transformation conditions are as follows: a pH value of 7.5-8.5, a transformation temperature of 28-32° C., and a rotation speed of 150-250 rpm.

Preferably, the whole-cell of the recombinant *Escherichia coli* is obtained by performing induced fermentation on the recombinant *Escherichia coli*, and specifically, a single colony of the recombinant *Escherichia coli* is inoculated in a seed culture medium with ampicillin and kanamycin resistance to culture overnight under 35-38° C. and 180-220 rpm to obtain a seed solution. The seed solution is transferred into a fermentation culture medium with ampicillin and kanamycin resistance in inoculation amount of 1-5% (v/v) to culture under 35-38° C. and 180-220 rpm until OD600 is 0.6-0.8. IPTG with a final concentration of 0.5-1.5 mM is added to induce for 10-15 h under 22-28° C. and 180-220 rpm to obtain a fermentation liquor. The fermentation liquor is centrifuged to collect a bacterial cell, namely the whole-cell of the recombinant *Escherichia coli*.

Preferably, the seed culture medium includes 8-12 g/L of tryptone, 4-6 g/L of yeast powder, 8-12 g/L of sodium chloride, and the pH value is 7.0-7.2.

Preferably, the fermentation culture medium includes 10-15 g/L of tryptone, 20-25 g/L of yeast powder, 3-5 g/L of glycerol, 12-13 g/L of dipotassium phosphate and 2-3 g/L of monopotassium phosphate.

As compared with the prior art, the invention has the following beneficial effects:

A double-plasmid recombinant bacterium is constructed through molecular biological means for co-expressing the aldehyde synthase (AAS) gene, the amine oxidase Mao (gene) and the aldehyde dehydrogenase (Glox) gene. The constructed expression plasmids are introduced into the *Escherichia coli* to reconstruct to obtain a recombinant cell. A recombination strain for efficiently producing the glutarate is obtained through amicillin resistance and kanamycin resistance combined plate screening. Efficient production of the glutarate is achieved by optimizing concentration of a substrate, cell concentration and the transformation temperature. L-lysine with a concentration of 30 g/L may be transformed into 19.65 g of the glutarate through reactions for 30 h under the transformation conditions that the cell concentration is 30 g/L, a pH value is 8 and 6 mM of $NAD^+$ is additionally added, where a transformation rate may be 65.3%.

DETAILED DESCRIPTION OF THE PREFERRED EMBODIMENTS

The present invention will be further described below in conjunction with specific embodiments, so that those skilled in the art may better understand and implement the present invention, but the embodiments described here are not intended to limit the present invention.

Figure 1:
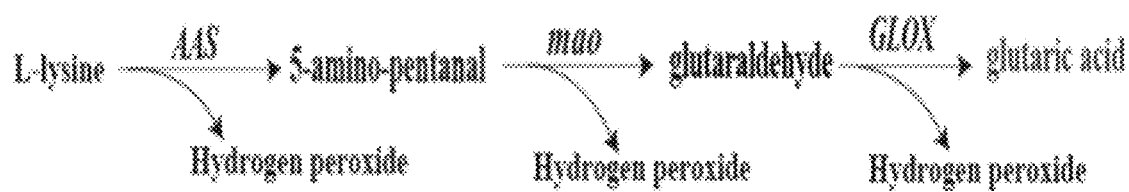
FIG. 1 shows a glutarate biosynthetic pathway.

Feasibility verification of metabolic pathway of the present invention: a constructed system, namely constructed recombinant *Escherichia coli*, can transform the L-lysine into glutarate with addition of a cofactor $NAD^+$. The specific reaction process is as shown in FIG. 1.

In the present invention, the pETM6R1 plasmid, the pET28a plasmid, the RSF plasmid, the pCOR plasmid, the pCDF plasmid and the PACYC plasmid are commercially available.

In the present invention, *E. coli* BL21(DE3), *E. coli* JM109 (DE3) and *E. coli* MG1655 (DE3) are commercially available.

In the present invention, the seed culture medium includes 10 g/L of tryptone, 5 g/L of yeast powder, 10 g/L of sodium chloride, and the pH value is 7.0-7.2.

The fermentation culture medium includes 12 g/L of tryptone, 24 g/L of yeast powder, 4 g/L of glycerol, 12.53 g/L of dipotassium phosphate and 2.31 g/L of monopotassium phosphate.

In the present invention, the detection method of the glutarate utilizes a HPLC system, an organic acid analytical column (Amine HPX-87H column, 300 mm 7.8 mm) and an ultraviolet detector (210 nm), and 5 mm $H_2SO_4$ as a mobile phase. The flow rate of the mobile phase is 0.6 mL/min, and the temperature is kept at 60° C. during operation.

Embodiment 1: Construction of Recombinant Plasmid pETM6R1-AAS-Mao

A coding gene of aromatic aldehyde synthase (AAS) with an amino acid sequence as shown in SEQ ID NO:1 and a coding gene of amine oxidase (Mao) with an amino acid sequence as shown in SEQ ID NO:2 were amplified to obtain DNA fragments containing the coding gene of the aromatic aldehyde synthase (AAS) and DNA fragments containing the coding gene of the amine oxidase (Mao). The pETM6R1 plasmid was enzyme digested overnight by the restriction endonuclease XhoI to obtain a linearized vector and a sticky end is exposed. The purified DNA fragments containing the coding gene of the aromatic aldehyde synthase (AAS) and the purified DNA fragments containing the coding gene of the amine oxidase (Mao) were ligated to a pETM6R1 vector through enzyme digestion to reconstruct a recombinant plasmid pETM6R1-AAS-Mao. The reconstructed recombinant plasmid pETM6R1-AAS-Mao was transformed into *E. coli* JM109 competent cells through a chemical transformation method, and the competent cells were cultured for 12 h in an LB flat plate containing ampicillin. PCR verification was performed on a bacterial colony grown on the flat plate. A positive transformant was selected and inoculated into an LB culture medium, and a plasmid was extracted after culturing for 12 h at 37° C. A recombinant plasmid pETM6R1-AAS-Mao was constructed through sequencing verification.

Embodiment 2: Construction of the Recombinant Plasmid pET28a-Glox

A coding gene of aldehyde dehydrogenase (Glox) with an amino acid sequence as shown in SEQ ID NO:3 was amplified to obtain DNA fragments containing the coding gene of the aldehyde dehydrogenase (Glox); the restriction endonucleases BamHI and XhoI were selected for performing double-enzyme digestion on a vector pET28a for 3 h at 37° C. to obtain a linearized vector and a sticky end was exposed. The recycled Glox coding gene was ligated with the plasmid pET28a for 10 h at 16° C. through T4 ligase to reconstruct a recombinant plasmid pET28a-Glox. The constructed recombinant plasmid pET28a-Glox was transformed into E. coli JM109 competent cells through a chemical transformation method, and the competent cells were cultured for 12 h in an LB flat plate containing kanamycin. PCR verification was performed on a bacterial colony grown on the flat plate. A positive transformant was selected and inoculated into an LB culture medium, and a plasmid was extracted after culturing for 12 h at 37° C. A recombinant plasmid pET28a-Glox was constructed through sequencing verification.

Embodiment 3: Construction and Expression of Double-Plasmid Recombinant Escherichia coli The recombinant plasmid pETM6R1-AAS-Mao constructed in Embodiment 1 and the recombinant plasmid pET28a-Glox constructed in Embodiment 2 were simultaneously transformed into E. coli MG1655 (DE3) competent cells through a chemical transformation method. The competent cells were cultured for 12 h in an LB flat plate with ampicillin resistance and kanamycin resistance. A single colony grown on the flat plate was inoculated into a seed culture medium with ampicillin resistance and kanamycin resistance to culture overnight under 37° C. and 200 rpm. The single colony was transferred into a 100 mL fermentation culture medium with ampicillin resistance and kanamycin resistance at inoculation amount of 2% (v/v), and was culture under 37° C. and 200 rpm until OD600 was 0.6-0.8. IPTG with a final concentration of 1 mM was added for inducing for 12 h under 25° C. and 200 rpm, and the bacterial cells were collected by centrifuging for whole-cell transformation.

Embodiment 4: Verification of Whole-Cell Transformation of Double-Plasmid Recombinant Escherichia coli A PBS buffer solution was taken as a medium for whole-cell transformation, and transformation conditions were as follows:

Wet cells of the recombinant Escherichia coli obtained in Embodiment 3 was centrifuged and used as a catalyst for the whole-cell transformation. Reaction liquid was obtained by rotating for 30 h at 30° C. when the concentration of L-lysine was 30 g/L, the pH value was 8, a rotation speed of a shaker was 220 rpm, a concentration of the cell was 30 g/L. After being centrifuged for 5 min at 12000 rpm, the reaction liquid was filtered by a 0.22 μm filter membrane, was diluted by 10 times and was detected by HPLC. To further verify reliability of the result, the glutarate in the reaction liquid was detected through LC-MS.

Figure 2:
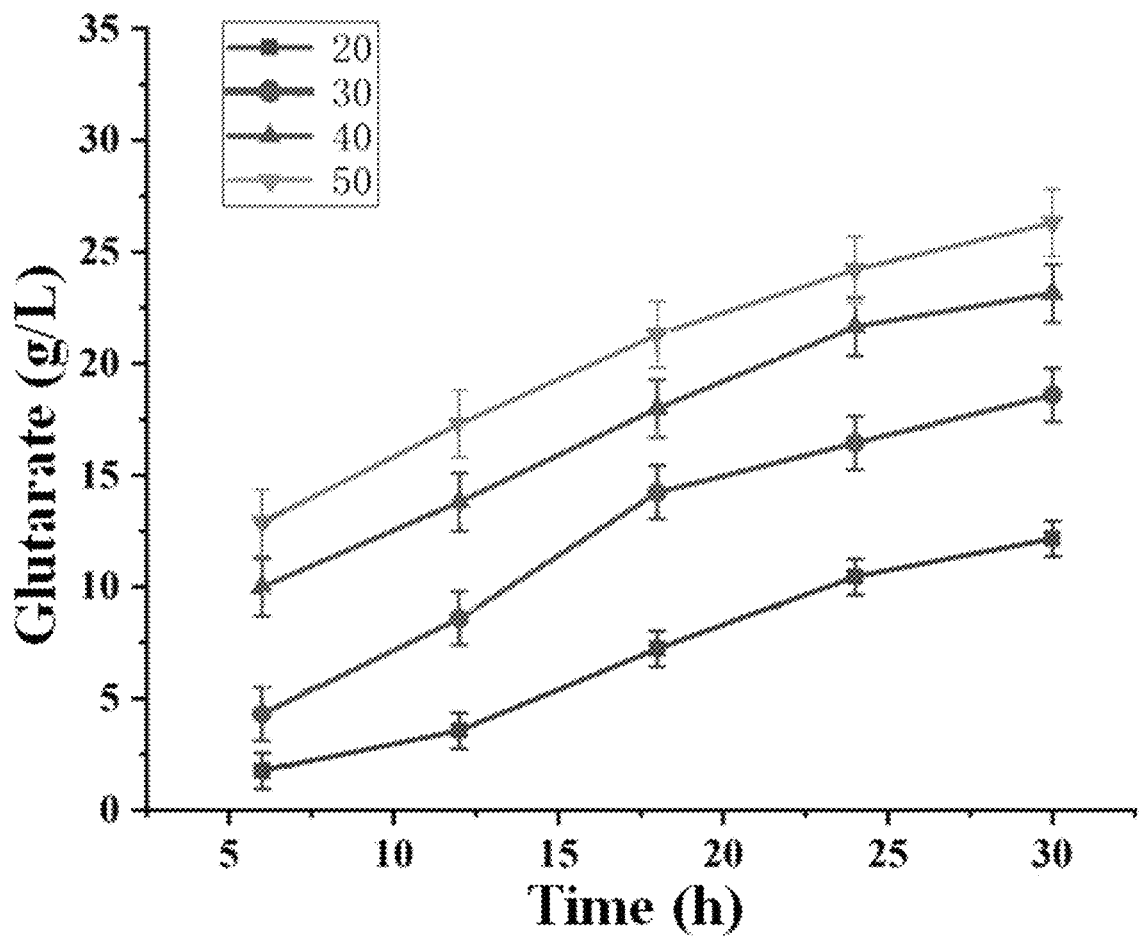
FIG. 2 shows the effect of substrate concentration on yield of glutarate.

Embodiment 5: Optimization of Substrate Concentration for Whole-Cell Transformation of Recombinant Escherichia coli A bacterial strain with a concentration of 30 g/L was added into a 10 mL reaction system, where concentrations of L-lysine was respectively 20 g/L, 30 g/L, 40 g/L and 50 g/L, the pH value was 8, a rotation speed of a shaker was 220 rpm, and transformation lasted for 30 h at 30° C., and the result was as shown in FIG. 2. When the concentration of L-lysine was 30 g/L, the transformation rate was the highest, up to 60.53%, and the yield was up to 18.59 g.

Figure 3:
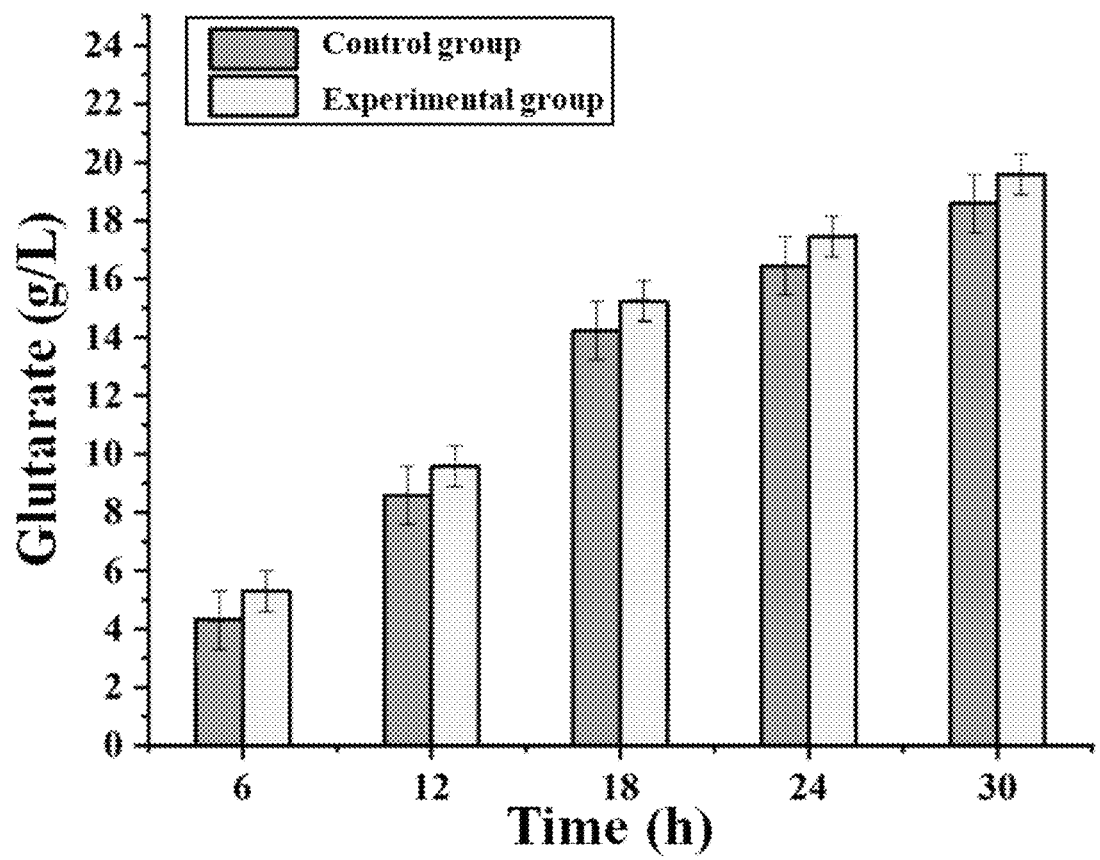
FIG. 3 shows the effect of $NAD^+$ on yield of glutarate.

Embodiment 6: Optimization of Cofactor for Whole-Cell Transformation of Recombinant Escherichia coli A bacterial strain with a concentration of 30 g/L was added into a 10 mL reaction system, where 6 mM of NAD+ was additionally added, the pH value was 8, a rotation speed of a shaker was 220 rpm, transformation lasted for 30 h at 30° C., and the result was as shown in FIG. 3. When $NAD^+$ was additionally added, the transformation rate was increased to 65.3%, and the yield was 19.65 g.

Embodiment 7: Construction and Expression of Recombinant Expression Vectors pETM6R1-AAS-MAO, PRSF-AAS-MAO and pCOR-AAS-MAO On the basis of successfully constructed expression vectors, pathway enzyme was assembled through the ePathBrick technology. The steps were introduced by taking the construction of the recombinant expression vector pETM6R1-AAS-MAO as an example. The restriction endonuclease XhoI was used to obtain a linearized vector and a sticky end was exposed; then, a target gene with the sticky end was then obtained; and finally, the target gene was ligated overnight at 16° C. through T4 ligase, the product was transformed into JM109 competent cells, and a single colony was selected for PCR verification; and the recombinant expression vector pETM6R1-AAS-MAO was successfully constructed if the stripe size was correct, and construction methods of the other two recombinant expression vectors were kept consistent. In such a manner, 3 recombinant expression vectors were obtained, which were respectively pETM6R1-AAS-MAO, PRSF-AAS-MAO and pCOR-AAS-MAO.

Embodiment 8: Construction and Expression of Recombinant Expression Vectors pET28a-GLOX, pCDF-GLOX and PACYC-GLOX On the basis of successfully constructed expression vectors, pathway enzyme was assembled through the ePathBrick technology. The steps were introduced by taking the construction of the recombinant expression vector pET28a-GLOX as an example. The restriction endonucleases BamHI and XhoI were used to perform double enzyme-digestion on a vector pET28a to obtain a linearized vector and a sticky end was exposed; then, a target gene with the sticky end was then obtained; and finally, the target gene was ligated overnight at 16° C. through T4 ligase, the product was transformed into JM109 competent cells, and a single colony was selected for PCR verification; and the recombinant expression vector pET28a-GLOX was successfully constructed if the stripe size was correct, and construction methods of the other two recombinant expression vectors were kept consistent. In such a manner, 3 recombinant expression vectors were obtained, which were respectively pET28a-GLOX, pCDF-GLOX and PACYC-GLOX.

Embodiment 9: Construction and Expression of Recombinant Host

According to a scheme of simultaneously expressing an aromatic aldehyde synthase (AAS) gene, an amine oxidase (Mao) gene and an aldehyde dehydrogenase (Glox) gene, the plasmids constructed in Embodiment 8 and Embodiment 9 were respectively transformed into competent cells through a chemical transformation method. The competent cells were respectively *E. coli* BL21 (DE3), *E. coli* JM109 (DE3) and *E. coli* MG1655 (DE3), and a specific combination way of the recombinant expression vectors and a host bacterium is shown in table 1. The constructed recombinant strains were respectively cultured for 12 h in an LB flat plate with resistance, and a single colony grown on the flat plate was inoculated into a seed culture medium with resistance to culture overnight under 37° C. and 200 rpm. The single colony was transferred into a 100 mL fermentation culture medium with ampicillin resistance and kanamycin resistance at an inoculation amount of 2% (v/v), and was cultured under 37° C. and 200 rpm until $OD_{600}$ was 0.6-0.8. IPTG with a final concentration of 1 mM was added for inducing for 12 h under 25° C. and 200 rpm, and cells were collected for whole-cell transformation.

TABLE 1

| No. | Host | Double vectors |
| --- | --- | --- |
| 1 | *E. coli* BL21 | pETM6R1-AAS-MAO&pET28a-GLOX |
| 2 | (DE3) | PRSF-AAS-MAO&pET28a-GLOX |
| 3 | | pCOR-AAS-MAO&pET28a-GLOX |
| 4 | | pETM6R1-AAS-MAO&pCDF-GLOX |
| 5 | | PRSF-AAS-MAO&pCDF-GLOX |
| 6 | | pCOR-AAS-MAO&pCDF-GLOX |
| 7 | | pETM6R1-AAS-MAO&PACYC-GLOX |
| 8 | | PRSF-AAS-MAO&PACYC-GLOX |
| 9 | | pCOR-AAS-MAO&PACYC-GLOX |
| 10 | *E. coli* JM109 | pETM6R1-AAS-MAO&pET28a-GLOX |
| 11 | (DE3) | PRSF-AAS-MAO&pET28a-GLOX |
| 12 | | pCOR-AAS-MAO&pET28a-GLOX |

TABLE 1-continued

| No. | Host | Double vectors |
| --- | --- | --- |
| 13 | | pETM6R1-AAS-MAO&pCDF-GLOX |
| 14 | | PRSF-AAS-MAO&pCDF-GLOX |
| 15 | | pCOR-AAS-MAO&pCDF-GLOX |
| 16 | | pETM6R1-AAS-MAO&PACYC-GLOX |
| 17 | | PRSF-AAS-MAO&PACYC-GLOX |
| 18 | | pCOR-AAS-MAO&PACYC-GLOX |
| 19 | *E. coli* | pETM6R1-AAS-MAO&pET28a-GLOX |
| 20 | MG1655 | PRSF-AAS-MAO&pET28a-GLOX |
| 21 | (DE3) | pCOR-AAS-MAO&pET28a-GLOX |
| 22 | | pETM6R1-AAS-MAO&pCDF-GLOX |
| 23 | | PRSF-AAS-MAO&pCDF-GLOX |
| 24 | | pCOR-AAS-MAO&pCDF-GLOX |
| 25 | | pETM6R1-AAS-MAO&PACYC-GLOX |
| 26 | | PRSF-AAS-MAO&PACYC-GLOX |
| 27 | | pCOR-AAS-MAO&PACYC-GLOX |

Embodiment 10

Figure 4:
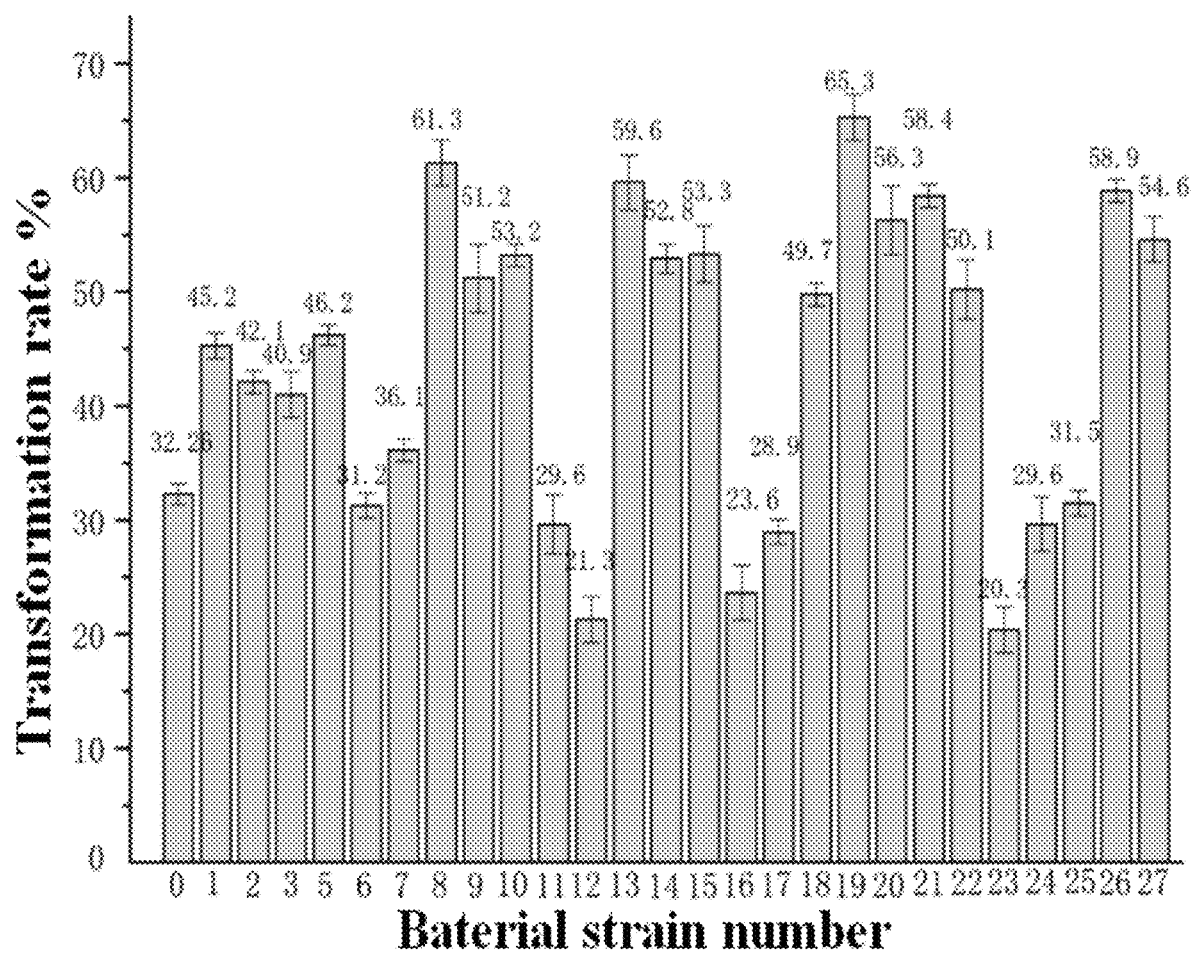
FIG. 4 shows the transformation rate for transforming whole-cells of different bacterial strains.

A PBS buffer solution was taken as a medium for whole-cell transformation, and transformation conditions were as follows:

Wet cells of 27 recombinant bacteria obtained in Embodiment 9 were respectively selected, centrifuged and used as a catalyst for the whole-cell transformation. When the concentration of the L-lysine was 30 g/L, the cell concentration was 30 g/L, and 6 mM of NAD+ was additionally added, the pH value was 8, the rotation speed of a shaker was 220 rpm, and rotation lasts for 30 h at 30° C. After being centrifuged for 5 min at 12000 rpm, the reaction liquid was filtered by a 0.22 μm filter membrane, was diluted by 10 times and was detected by HPLC, where the transformation rate was as shown in FIG. 4. The above recombinant bacterial strains were used as a catalyst for whole-cell transformation, and L-lysine was transformed into glutarate. For the transformation rate, there was certain difference among the bacterial strains. The transformation rate of the recombinant bacterium constructed in Embodiment 3 of the present invention was the highest, up to 65.3%.

The above embodiments are only preferred embodiments for a detailed description of the present invention, and the protection scope of the present invention is not limited thereto. Equivalent substitutions or alterations made by those skilled in the art on the basis of the present invention are all within the protection scope of the present invention. The protection scope of the present invention shall be defined by the Claims.

What is claimed is:

1. A recombinant *Escherichia coli* for producing glutarate, wherein the recombinant *Escherichia coli* is obtained by recombinantly expressing an aromatic aldehyde synthase (AAS) gene, amine oxidase (Mao) gene and aldehyde dehydrogenase (Glox) gene in a host of *Escherichia coli*.

2. The recombinant *Escherichia coli* according to claim 1, wherein the aromatic aldehyde synthase (AAS) gene, the amine oxidase (Mao) gene and the aldehyde dehydrogenase (Glox) gene are expressed through a double-plasmid expression system, and the aromatic aldehyde synthase gene and the amine oxidase gene are expressed through the same plasmid.

3. The recombinant *Escherichia coli* according to claim 2, wherein the double-plasmid expression system is a combination of two of a pETM6R1 plasmid, pET28a plasmid, a PRSF plasmid, a pCOR plasmid, a pCDF plasmid and a PACYC plasmid.

4. The recombinant *Escherichia coli* according to claim 1, wherein an amino acid sequence of the aromatic aldehyde synthase comprises SEQ ID NO: 1, an amino acid sequence of the amine oxidase (Mao) comprises SEQ ID NO: 2, and an amino acid sequence of the aldehyde dehydrogenase (Glox) comprises SEQ ID NO:3.

5. The recombinant *Escherichia coli* according to claim 1, wherein the host of the *Escherichia coli* is *E. coli* BL21 (DE3), *E. coli* JM109 (DE3) or *E. coli* MG1655 (DE3).

6. A construction method of the recombinant *Escherichia coli* according to claim 1, comprising steps of:
S1, ligating the aromatic aldehyde synthase (AAS) gene and the amine oxidase (Mao) gene to a first vector to obtain a first recombinant vector;
S2, ligating the aldehyde dehydrogenase (Glox) gene to a second vector to obtain a second recombinant vector;
S3, introducing the first recombinant vector and the second recombinant vector into plural initial *Escherichia coli* host cells to produce constructed recombinant strains, and screening the constructed recombinant strains to identify a constructed recombinant strain that is capable of expressing the aromatic aldehyde synthase (AAS) gene, the amine oxidase (Mao) gene and aldehyde dehydrogenase (Glox) gene as the recombinant *Escherichia coli* for producing glutarate.

7. A method for producing glutarate, comprising:
providing the recombinant *Escherichia coli* according to claim 1; and
reacting L-lysine to produce glutarate in the presence of the recombinant *Escherichia coli* in a catalytic system.

8. The method according to claim 7, wherein a concentration of L-lysine in the catalytic system.

9. The method according to claim 7, wherein the catalytic system further comprises 4-8 nM of $NAD^+$.

10. The method according to claim 7, wherein the catalytic system has a pH value of 7.5-8.5 and a temperature of 28-32° C., and the reacting is performed while shaking the catalytic system at a rotation speed of 150-250 rpm.

* * * * *

SEQUENCE LISTING

```
<160> NUMBER OF SEQ ID NOS: 3

<210> SEQ ID NO 1
<211> LENGTH: 514
<212> TYPE: PRT
<213> ORGANISM: Artificial sequence
<220> FEATURE:
<223> OTHER INFORMATION: Aromatic aldehyde synthase

<400> SEQUENCE: 1

Met Gly Ser Ile Asp Asn Leu Thr Glu Lys Leu Ala Ser Gln Phe Pro
1               5                   10                  15

Met Asn Thr Leu Glu Pro Glu Glu Phe Arg Arg Gln Gly His Met Met
            20                  25                  30

Ile Asp Phe Leu Ala Asp Tyr Tyr Arg Lys Val Glu Asn Tyr Pro Val
```

```
            35                  40                  45
Arg Ser Gln Val Ser Pro Gly Tyr Leu Arg Glu Ile Leu Pro Glu Ser
 50                  55                  60

Ala Pro Tyr Asn Pro Glu Ser Leu Glu Thr Ile Leu Gln Asp Val Gln
 65                  70                  75                  80

Thr Lys Ile Ile Pro Gly Ile Thr His Trp Gln Ser Pro Asn Phe Phe
                     85                  90                  95

Ala Tyr Phe Pro Ser Ser Gly Ser Thr Ala Gly Phe Leu Gly Glu Met
            100                 105                 110

Leu Ser Thr Gly Phe Asn Val Gly Phe Asn Trp Met Val Ser Pro
            115                 120                 125

Ala Ala Thr Glu Leu Glu Asn Val Val Thr Asp Trp Phe Gly Lys Met
    130                 135                 140

Leu Gln Leu Pro Lys Ser Phe Leu Phe Ser Gly Gly Gly Gly Val
145                 150                 155                 160

Leu Gln Gly Thr Thr Cys Glu Ala Ile Leu Cys Thr Leu Val Ala Ala
                    165                 170                 175

Arg Asp Lys Asn Leu Arg Gln His Gly Met Asp Asn Ile Gly Lys Leu
                    180                 185                 190

Val Val Tyr Cys Ser Asp Gln Thr His Ser Ala Leu Gln Lys Ala Ala
            195                 200                 205

Lys Ile Ala Gly Ile Asp Pro Lys Asn Phe Arg Ala Ile Glu Thr Thr
    210                 215                 220

Lys Ser Ser Asn Phe Gln Leu Cys Pro Lys Arg Leu Glu Ser Ala Ile
225                 230                 235                 240

Leu His Asp Leu Gln Asn Gly Leu Ile Pro Leu Tyr Leu Cys Ala Thr
                    245                 250                 255

Val Gly Thr Thr Ser Ser Thr Thr Val Asp Pro Leu Pro Ala Leu Thr
            260                 265                 270

Glu Val Ala Lys Lys Tyr Asp Leu Trp Val His Val Asp Ala Ala Tyr
    275                 280                 285

Ala Gly Ser Ala Cys Ile Cys Pro Glu Phe Arg Gln Tyr Leu Asp Gly
290                 295                 300

Val Glu Asn Ala Asp Ser Phe Ser Leu Asn Ala His Lys Trp Phe Leu
305                 310                 315                 320

Thr Thr Leu Asp Cys Cys Cys Leu Trp Val Arg Asn Pro Ser Ala Leu
                    325                 330                 335

Ile Lys Ser Leu Ser Thr Tyr Pro Glu Phe Leu Lys Asn Asn Ala Ser
            340                 345                 350

Glu Thr Asn Lys Val Val Asp Tyr Lys Asp Trp Gln Ile Met Leu Ser
    355                 360                 365

Arg Arg Phe Arg Ala Leu Lys Leu Trp Phe Val Leu Arg Ser Tyr Gly
370                 375                 380

Val Gly Gln Leu Arg Glu Phe Ile Arg Gly His Val Gly Met Ala Lys
385                 390                 395                 400

Tyr Phe Glu Gly Leu Val Asn Met Asp Lys Arg Phe Glu Val Val Ala
                    405                 410                 415

Pro Arg Leu Phe Ser Met Val Cys Phe Arg Ile Lys Pro Ser Ala Met
            420                 425                 430

Ile Gly Lys Asn Asp Glu Asp Glu Val Asn Glu Ile Asn Arg Lys Leu
    435                 440                 445

Leu Glu Ser Val Asn Asp Ser Gly Arg Ile Tyr Val Ser His Thr Val
450                 455                 460
```

-continued

```
Leu Gly Gly Ile Tyr Val Ile Arg Phe Ala Ile Gly Thr Leu Thr
465                 470                 475                 480

Asp Ile Asn His Val Ser Ala Ala Trp Lys Val Leu Gln Asp His Ala
                485                 490                 495

Gly Ala Leu Leu Asp Asp Thr Phe Thr Ser Asn Lys Leu Val Glu Val
            500                 505                 510

Leu Ser

<210> SEQ ID NO 2
<211> LENGTH: 527
<212> TYPE: PRT
<213> ORGANISM: Artificial sequence
<220> FEATURE:
<223> OTHER INFORMATION: Amine oxidase

<400> SEQUENCE: 2

Met Glu Asn Gln Glu Lys Ala Ser Ile Ala Gly His Met Phe Asp Val
1               5                   10                  15

Val Val Ile Gly Gly Ile Ser Gly Leu Ser Ala Ala Lys Leu Leu
            20                  25                  30

Thr Glu Tyr Gly Val Ser Val Leu Val Leu Glu Ala Arg Asp Arg Val
            35                  40                  45

Gly Gly Arg Thr Tyr Thr Ile Arg Asn Glu His Val Asp Tyr Val Asp
        50                  55                  60

Val Gly Gly Ala Tyr Val Gly Pro Thr Gln Asn Arg Ile Leu Arg Leu
65              70                  75                  80

Ser Lys Glu Leu Gly Ile Glu Thr Tyr Lys Val Asn Val Ser Glu Arg
                85                  90                  95

Leu Val Gln Tyr Val Lys Gly Lys Thr Tyr Pro Phe Arg Gly Ala Phe
            100                 105                 110

Pro Pro Val Trp Asn Pro Ile Ala Tyr Leu Asp Tyr Asn Asn Leu Trp
        115                 120                 125

Arg Thr Ile Asp Asn Met Gly Lys Glu Ile Pro Thr Asp Ala Pro Trp
130                 135                 140

Glu Ala Gln His Ala Asp Lys Trp Asp Lys Met Thr Met Lys Glu Leu
145                 150                 155                 160

Ile Asp Lys Ile Cys Trp Thr Lys Thr Ala Arg Arg Phe Ala Tyr Leu
                165                 170                 175

Phe Val Asn Ile Asn Val Thr Ser Glu Pro His Glu Val Ser Ala Leu
            180                 185                 190

Trp Phe Leu Trp Tyr Val Lys Gln Cys Gly Gly Thr Thr Arg Ile Phe
        195                 200                 205

Ser Val Thr Asn Gly Gly Gln Glu Arg Lys Phe Val Gly Gly Ser Gly
210                 215                 220

Gln Val Ser Glu Arg Ile Met Asp Leu Leu Gly Asp Gln Val Lys Leu
225                 230                 235                 240

Asn His Pro Val Thr His Val Asp Gln Ser Ser Asp Asn Ile Ile Ile
                245                 250                 255

Glu Thr Leu Asn His Glu His Tyr Glu Cys Lys Tyr Val Ile Asn Ala
            260                 265                 270

Ile Pro Pro Thr Leu Thr Ala Lys Ile His Phe Arg Pro Glu Leu Pro
        275                 280                 285

Ala Glu Arg Asn Gln Leu Ile Gln Arg Leu Pro Met Gly Ala Val Ile
    290                 295                 300
```

Lys Cys Met Met Tyr Tyr Lys Glu Ala Phe Trp Lys Lys Lys Asp Tyr
305                 310                 315                 320

Cys Gly Cys Met Ile Ile Glu Asp Glu Asp Ala Pro Ile Ser Ile Thr
                325                 330                 335

Leu Asp Asp Thr Lys Pro Asp Gly Ser Leu Pro Ala Ile Met Gly Phe
            340                 345                 350

Ile Leu Ala Arg Lys Ala Asp Arg Leu Ala Lys Leu His Lys Glu Ile
            355                 360                 365

Arg Lys Lys Ile Cys Glu Leu Tyr Ala Lys Val Leu Gly Ser Gln
    370                 375                 380

Glu Ala Leu His Pro Val His Tyr Glu Glu Lys Asn Trp Cys Glu Glu
385                 390                 395                 400

Gln Tyr Ser Gly Gly Cys Tyr Thr Ala Tyr Phe Pro Pro Gly Ile Met
                405                 410                 415

Thr Gln Tyr Gly Arg Val Ile Arg Gln Pro Val Gly Arg Ile Phe Phe
            420                 425                 430

Ala Gly Thr Glu Thr Ala Thr Lys Trp Ser Gly Tyr Met Glu Gly Ala
        435                 440                 445

Val Glu Ala Gly Glu Arg Ala Ala Arg Glu Val Leu Asn Gly Leu Gly
450                 455                 460

Lys Val Thr Glu Lys Asp Ile Trp Val Gln Glu Pro Glu Ser Lys Asp
465                 470                 475                 480

Val Pro Ala Val Glu Ile Thr His Thr Phe Trp Glu Arg Asn Leu Pro
                485                 490                 495

Ser Val Ser Gly Leu Leu Lys Ile Gly Phe Ser Thr Ser Val Thr
                500                 505                 510

Ala Leu Gly Phe Val Leu Tyr Lys Tyr Lys Leu Leu Pro Arg Ser
        515                 520                 525

<210> SEQ ID NO 3
<211> LENGTH: 485
<212> TYPE: PRT
<213> ORGANISM: Artificial sequence
<220> FEATURE:
<223> OTHER INFORMATION: Aldehyde dehydrogenase

<400> SEQUENCE: 3

Met Glu Leu Glu Val Arg Arg Val Arg Gln Ala Phe Leu Ser Gly Arg
1               5                   10                  15

Ser Arg Pro Leu Arg Phe Arg Leu Gln Gln Leu Glu Ala Leu Arg Arg
            20                  25                  30

Met Val Gln Glu Arg Glu Lys Asp Ile Leu Thr Ala Ile Ala Ala Asp
        35                  40                  45

Leu Cys Lys Ser Glu Phe Asn Val Tyr Ser Gln Glu Val Ile Thr Val
50                  55                  60

Leu Gly Glu Ile Asp Phe Met Leu Glu Asn Leu Pro Glu Trp Val Thr
65                  70                  75                  80

Ala Lys Pro Val Lys Lys Asn Val Leu Thr Met Leu Asp Glu Ala Tyr
                85                  90                  95

Ile Gln Pro Gln Pro Leu Gly Val Val Leu Ile Ile Gly Ala Trp Asn
            100                 105                 110

Tyr Pro Phe Val Leu Thr Ile Gln Pro Leu Ile Gly Ala Ile Ala Ala
        115                 120                 125

Gly Asn Ala Val Ile Ile Lys Pro Ser Glu Leu Ser Glu Asn Thr Ala
    130                 135                 140

-continued

```
Lys Ile Leu Ala Lys Leu Leu Pro Gln Tyr Leu Asp Gln Asp Leu Tyr
145                 150                 155                 160

Ile Val Ile Asn Gly Gly Val Glu Glu Thr Thr Glu Leu Leu Lys Gln
                165                 170                 175

Arg Phe Asp His Ile Phe Tyr Thr Gly Asn Thr Ala Val Gly Lys Ile
                180                 185                 190

Val Met Glu Ala Ala Ala Lys His Leu Thr Pro Val Thr Leu Glu Leu
            195                 200                 205

Gly Gly Lys Ser Pro Cys Tyr Ile Asp Lys Asp Cys Asp Leu Asp Ile
        210                 215                 220

Val Cys Arg Arg Ile Thr Trp Gly Lys Tyr Met Asn Cys Gly Gln Thr
225                 230                 235                 240

Cys Ile Ala Pro Asp Tyr Ile Leu Cys Glu Ala Ser Leu Gln Asn Gln
                245                 250                 255

Ile Val Trp Lys Ile Lys Glu Thr Val Lys Glu Phe Tyr Gly Glu Asn
                260                 265                 270

Ile Lys Glu Ser Pro Asp Tyr Gly Arg Ile Ile Asn Leu Arg His Phe
            275                 280                 285

Lys Arg Ile Leu Ser Leu Leu Glu Gly Gln Lys Ile Ala Phe Gly Gly
        290                 295                 300

Glu Thr Asp Glu Ala Thr Arg Tyr Ile Ala Pro Thr Val Leu Thr Asp
305                 310                 315                 320

Val Asp Pro Lys Thr Lys Val Met Gln Glu Glu Ile Phe Gly Pro Ile
                325                 330                 335

Leu Pro Ile Val Pro Val Lys Asn Val Asp Glu Ala Ile Asn Phe Ile
                340                 345                 350

Asn Glu Arg Glu Lys Pro Leu Ala Leu Tyr Val Phe Ser His Asn His
            355                 360                 365

Lys Leu Ile Lys Arg Met Ile Asp Glu Thr Ser Ser Gly Gly Val Thr
        370                 375                 380

Gly Asn Asp Val Ile Met His Phe Thr Leu Asn Ser Phe Pro Phe Gly
385                 390                 395                 400

Gly Val Gly Ser Ser Gly Met Gly Ala Tyr His Gly Lys His Ser Phe
                405                 410                 415

Asp Thr Phe Ser His Gln Arg Pro Cys Leu Leu Lys Ser Leu Lys Arg
            420                 425                 430

Glu Gly Ala Asn Lys Leu Arg Tyr Pro Pro Asn Ser Gln Ser Lys Val
        435                 440                 445

Asp Trp Gly Lys Phe Phe Leu Leu Lys Arg Phe Asn Lys Glu Lys Leu
450                 455                 460

Gly Leu Leu Leu Leu Thr Phe Leu Gly Ile Val Ala Ala Val Leu Val
465                 470                 475                 480

Lys Ala Glu Tyr Tyr
                485
```